United States Patent
Jacquemyns

(10) Patent No.: US 10,144,100 B2
(45) Date of Patent: Dec. 4, 2018

(54) METHOD OF PREPARATION FOR RESTORING TOOTH STRUCTURE

(71) Applicant: Viax Dental Technologies, LLC, Hallandale Beach, FL (US)

(72) Inventor: Evelyne Jacquemyns, Sint-Martens-Latem (BE)

(73) Assignee: Viax Dental Technologies, LLC, Hallandale Beach, FL (US)

( * ) Notice: Subject to any disclaimer, the term of this patent is extended or adjusted under 35 U.S.C. 154(b) by 687 days.

(21) Appl. No.: 14/170,120

(22) Filed: Jan. 31, 2014

(65) Prior Publication Data

US 2014/0215804 A1    Aug. 7, 2014

Related U.S. Application Data

(63) Continuation of application No. 12/698,777, filed on Feb. 2, 2010, now Pat. No. 8,640,338, which is a continuation-in-part of application No. 12/364,216, filed on Feb. 2, 2009, now abandoned.

(51) Int. Cl.
*B23P 19/04* (2006.01)
*A61C 1/08* (2006.01)
*B33Y 80/00* (2015.01)

(52) U.S. Cl.
CPC .............. *B23P 19/04* (2013.01); *A61C 1/082* (2013.01); *B33Y 80/00* (2014.12); *Y10T 29/49* (2015.01); *Y10T 29/49567* (2015.01)

(58) Field of Classification Search
CPC ......... B23P 19/04; A61C 1/082; A61C 13/00; A61C 13/0006; Y10T 29/49; Y10T 29/49567
See application file for complete search history.

(56) References Cited

U.S. PATENT DOCUMENTS

| 472,004 A | 3/1892 | Sweet |
| 1,407,840 A | 2/1922 | Cruttenden |

(Continued)

FOREIGN PATENT DOCUMENTS

| AT | 12407 B | 7/1903 |
| AT | 13375 B | 9/1903 |

(Continued)

OTHER PUBLICATIONS

English Machine Translation of WO 2009000505A1, Thomas Engelhardt, Dec. 31, 2008.*

(Continued)

*Primary Examiner* — Sarang Afzali
(74) *Attorney, Agent, or Firm* — Lerner, David, Littenberg, Krumholz & Mentlik, LLP

(57) ABSTRACT

A method for producing a dentist tool includes simulation of predetermined horizontal, vertical, and tilt movements to be followed by a cutting tool to remove a predetermined part of tooth structure for further treatment of a tooth. An overlay is determined to fit the tooth by determining a first guiding edge within the overlay corresponding to the predetermined movements and determining a second guiding edge within the overlay spaced apart from the first guiding edge and corresponding to the predetermined movements. The first and second guiding edges are provided to contact the cutting tool so as to guide horizontal, vertical, and tilt movements of the cutting tool such that the cutting tool follows the predetermined horizontal, vertical, and tilt movements for removal of the predetermined part of tooth structure. The determined overlay is produced with the first and second guiding edges and such that it fits the tooth.

23 Claims, 3 Drawing Sheets

(56) References Cited

U.S. PATENT DOCUMENTS

| | | |
|---|---|---|
| 1,772,027 A | 8/1930 | Baumgarten |
| 2,303,475 A | 12/1942 | Karlstrom |
| 2,591,183 A | 4/1952 | Mintz |
| 2,597,661 A | 5/1952 | McPhee |
| 2,621,408 A | 12/1952 | Klein |
| 2,634,501 A | 4/1953 | Linet |
| 2,644,235 A | 7/1953 | Mintz |
| 2,675,615 A | 4/1954 | Rosenberg |
| 2,770,040 A | 11/1956 | Moyer |
| 2,986,816 A | 6/1961 | Zeman |
| 3,011,259 A | 12/1961 | Baum |
| 3,063,149 A | 11/1962 | Suga |
| 3,254,413 A | 6/1966 | Suga |
| 3,376,643 A | 4/1968 | Nealon |
| 3,407,503 A | 10/1968 | Nealon |
| 3,445,935 A * | 5/1969 | Marshall ............... A61C 1/082 433/51 |
| 3,508,334 A | 4/1970 | Weissman |
| 3,585,723 A | 6/1971 | Simor |
| 3,600,810 A | 8/1971 | Marshall et al. |
| 4,144,645 A | 3/1979 | Marshall |
| 4,473,354 A | 9/1984 | Rigaud et al. |
| 4,504,230 A | 3/1985 | Patch |
| 4,526,542 A | 7/1985 | Kochis |
| 4,744,757 A | 5/1988 | Adair et al. |
| 4,778,387 A | 10/1988 | Komatsu |
| 4,941,826 A | 7/1990 | Loran et al. |
| 4,997,369 A | 3/1991 | Shafir |
| 5,015,183 A | 5/1991 | Fenick |
| 5,118,294 A | 6/1992 | Kurer |
| 5,133,660 A | 7/1992 | Fenick |
| 5,192,207 A | 3/1993 | Rosellini |
| 5,224,049 A | 6/1993 | Mushabac |
| 5,257,184 A | 10/1993 | Mushabac |
| 5,343,391 A | 8/1994 | Mushabac |
| 5,347,454 A | 9/1994 | Mushabac |
| 5,359,511 A | 10/1994 | Schroeder et al. |
| 5,368,478 A | 11/1994 | Andreiko et al. |
| 5,431,562 A | 7/1995 | Andreiko et al. |
| 5,447,432 A | 9/1995 | Andreiko et al. |
| 5,448,472 A | 9/1995 | Mushabac |
| 5,454,717 A | 10/1995 | Andreiko et al. |
| 5,545,039 A | 8/1996 | Mushabac |
| 5,562,448 A | 10/1996 | Mushabac |
| 5,569,578 A | 10/1996 | Mushabac |
| 5,575,646 A | 11/1996 | Giannella |
| 5,575,656 A | 11/1996 | Hajjar |
| 5,641,287 A | 6/1997 | Gittleman |
| 5,725,376 A | 3/1998 | Poirier |
| 5,768,134 A | 6/1998 | Swaelens et al. |
| 5,800,168 A | 9/1998 | Cascione et al. |
| 5,813,859 A | 9/1998 | Hajjar et al. |
| 5,897,315 A | 4/1999 | Nakayama et al. |
| 5,975,893 A | 11/1999 | Chishti et al. |
| 6,030,211 A | 2/2000 | Sandhaus |
| 6,049,743 A | 4/2000 | Baba |
| 6,183,248 B1 | 2/2001 | Chishti et al. |
| 6,190,171 B1 | 2/2001 | Hajjar et al. |
| 6,213,770 B1 | 4/2001 | Kuhn |
| 6,254,639 B1 | 7/2001 | Peckitt |
| 6,257,892 B1 | 7/2001 | Worthington |
| 6,309,215 B1 | 10/2001 | Phan et al. |
| 6,382,975 B1 | 5/2002 | Poirier |
| 6,390,812 B1 | 5/2002 | Chishti et al. |
| 6,398,548 B1 | 6/2002 | Muhammad et al. |
| 6,406,292 B1 | 6/2002 | Chishti et al. |
| 6,447,296 B2 | 9/2002 | Worthington |
| 6,457,972 B1 | 10/2002 | Chishti et al. |
| 6,485,298 B2 | 11/2002 | Chishti et al. |
| 6,511,323 B1 | 1/2003 | Wilkinson |
| 6,527,550 B1 | 3/2003 | Hajjar et al. |
| 6,537,067 B1 | 3/2003 | Wennemann |
| 6,554,611 B2 | 4/2003 | Chishti et al. |
| 6,626,672 B1 | 9/2003 | Been |
| 6,641,340 B1 | 11/2003 | Hajjar et al. |
| 6,685,469 B2 | 2/2004 | Chishti et al. |
| 6,705,861 B2 | 3/2004 | Chishti et al. |
| 6,722,880 B2 | 4/2004 | Chishti et al. |
| 6,767,208 B2 | 7/2004 | Kaza |
| 6,786,726 B2 | 9/2004 | Lehmann et al. |
| 6,814,575 B2 | 11/2004 | Poirier |
| 6,957,118 B2 | 10/2005 | Kopelman et al. |
| 7,004,757 B2 | 2/2006 | Wilkinson |
| 7,059,850 B1 | 6/2006 | Phan et al. |
| 7,097,451 B2 | 8/2006 | Tang |
| 7,108,511 B1 | 9/2006 | Shatkin |
| 7,110,844 B2 | 9/2006 | Kopelman et al. |
| 7,121,825 B2 | 10/2006 | Chishti et al. |
| 7,123,767 B2 | 10/2006 | Jones et al. |
| 7,125,248 B2 | 10/2006 | Phan et al. |
| 7,134,874 B2 | 11/2006 | Chishti et al. |
| 7,140,877 B2 | 11/2006 | Kaza |
| 7,147,465 B2 | 12/2006 | Jung et al. |
| 7,172,424 B2 | 2/2007 | Wu |
| 7,245,977 B1 | 7/2007 | Simkins |
| 7,287,982 B2 | 10/2007 | Riley et al. |
| 7,331,786 B2 | 2/2008 | Poirier |
| 7,346,417 B2 | 3/2008 | Luth et al. |
| 7,357,637 B2 | 4/2008 | Liechtung |
| 7,367,801 B2 | 5/2008 | Saliger |
| 7,377,778 B2 | 5/2008 | Chishti et al. |
| 7,383,094 B2 | 6/2008 | Kopelman et al. |
| 7,384,266 B2 | 6/2008 | Wen |
| 7,393,211 B2 * | 7/2008 | Wilkinson ............... A61C 3/02 433/213 |
| 7,442,040 B2 | 10/2008 | Kuo |
| 7,474,307 B2 | 1/2009 | Chishti et al. |
| 7,476,100 B2 | 1/2009 | Kuo |
| 7,536,234 B2 | 5/2009 | Kopelman et al. |
| 7,555,403 B2 | 6/2009 | Kopelman et al. |
| 7,572,125 B2 | 8/2009 | Brajnovic |
| 7,590,462 B2 * | 9/2009 | Rubbert ................. A61C 7/00 433/24 |
| 7,653,455 B2 | 1/2010 | Cinader, Jr. |
| 7,658,610 B2 | 2/2010 | Knopp |
| 7,695,281 B2 | 4/2010 | Burger et al. |
| 7,708,557 B2 | 5/2010 | Rubbert |
| 7,734,368 B2 | 6/2010 | Kopelman et al. |
| 7,774,084 B2 | 8/2010 | Cinader, Jr. |
| 7,801,632 B2 | 9/2010 | Orth et al. |
| 7,802,987 B1 | 9/2010 | Phan |
| 7,837,469 B2 | 11/2010 | Chishti et al. |
| 7,845,942 B2 | 12/2010 | Wilkinson |
| 7,862,336 B2 | 1/2011 | Kopelman et al. |
| 7,866,980 B2 | 1/2011 | Poirier |
| 7,905,726 B2 | 3/2011 | Stumpel |
| 7,996,099 B2 | 8/2011 | Kopelman et al. |
| 8,011,927 B2 | 9/2011 | Berckmans, III et al. |
| 8,021,153 B2 | 9/2011 | Poirier |
| 8,038,440 B2 | 10/2011 | Swaelens et al. |
| 8,041,439 B2 | 10/2011 | Kopelman et al. |
| 8,043,091 B2 | 10/2011 | Schmitt |
| 8,099,268 B2 | 1/2012 | Kitching et al. |
| 8,170,327 B2 | 5/2012 | Glor et al. |
| 8,301,287 B2 | 10/2012 | Kopelman et al. |
| 8,359,114 B2 | 1/2013 | Steingart et al. |
| 8,359,115 B2 | 1/2013 | Kopelman et al. |
| 8,425,973 B2 | 4/2013 | Dunne |
| 8,449,296 B2 | 5/2013 | Liechtung |
| 8,454,362 B2 | 6/2013 | Rubbert |
| 8,454,365 B2 | 6/2013 | Boerjes et al. |
| 8,562,340 B2 | 10/2013 | Chishti et al. |
| 8,602,780 B2 | 12/2013 | Rubbert |
| 8,640,338 B2 | 2/2014 | Jacquemyns |
| 8,651,859 B2 | 2/2014 | Chishti et al. |
| 8,651,860 B2 | 2/2014 | Kwon |
| 8,721,329 B2 | 5/2014 | Hultgren et al. |
| 8,734,150 B2 | 5/2014 | Chishti et al. |
| 8,753,114 B2 | 6/2014 | Vuillemot |
| 8,753,118 B2 | 6/2014 | Randall |
| 8,803,958 B2 | 8/2014 | Zhang et al. |
| 8,807,999 B2 | 8/2014 | Kuo et al. |
| 8,828,287 B2 | 9/2014 | van der Zel |
| 8,897,526 B2 | 11/2014 | MacLeod et al. |

| | | |
|---|---|---|
| 8,926,327 B2 | 1/2015 | Massad |
| 8,954,181 B2 | 2/2015 | MacLeod et al. |
| 9,011,147 B2 | 4/2015 | Jacquemyns |
| 9,044,296 B2 | 6/2015 | Randall |
| 9,069,914 B2 | 6/2015 | Kopelman et al. |
| 9,089,388 B2 | 7/2015 | Zegarelli |
| 9,125,712 B2 | 9/2015 | Kraemer et al. |
| 9,161,824 B2 | 10/2015 | Chishti et al. |
| 9,168,114 B2 | 10/2015 | Jung et al. |
| 9,186,228 B2 | 11/2015 | Kopelman et al. |
| 9,208,531 B2 | 12/2015 | Boerjes et al. |
| 9,220,576 B2 | 12/2015 | Heinz et al. |
| 9,295,534 B2 | 3/2016 | Ruppert et al. |
| 9,299,192 B2 | 3/2016 | Kopelman |
| 9,320,575 B2 | 4/2016 | Chishti et al. |
| 9,411,910 B2 | 8/2016 | Methot |
| 9,579,170 B2 | 2/2017 | Van Lierde et al. |
| 2001/0036617 A1 | 11/2001 | Karmaker et al. |
| 2002/0160337 A1 | 10/2002 | Klein et al. |
| 2003/0008259 A1 | 1/2003 | Kuo et al. |
| 2003/0064346 A1 | 4/2003 | Wennemann |
| 2004/0043355 A1 | 3/2004 | Jonsson et al. |
| 2004/0248065 A1 | 12/2004 | Schneider |
| 2005/0014109 A1 | 1/2005 | Lim |
| 2005/0095554 A1 | 5/2005 | Wilkinson |
| 2005/0244782 A1 | 11/2005 | Chishti et al. |
| 2005/0282106 A1 | 12/2005 | Sussman et al. |
| 2006/0008777 A1 | 1/2006 | Peterson et al. |
| 2006/0127848 A1 | 6/2006 | Sogo et al. |
| 2007/0218423 A1 | 9/2007 | Sapian |
| 2007/0238068 A1 | 10/2007 | Comfortes |
| 2007/0292821 A1 | 12/2007 | De Vreese |
| 2008/0085490 A1 | 4/2008 | Jabri |
| 2008/0153067 A1 | 6/2008 | Berckmans et al. |
| 2008/0176187 A1 | 7/2008 | Stumpel |
| 2008/0259411 A1 | 10/2008 | Karlsson |
| 2008/0287953 A1 | 11/2008 | Sers |
| 2008/0312659 A1 | 12/2008 | Metzger et al. |
| 2008/0318187 A1 | 12/2008 | Wilkinson |
| 2009/0004629 A1 | 1/2009 | Fishman et al. |
| 2009/0263764 A1 | 10/2009 | Berckmans, III et al. |
| 2009/0291417 A1 | 11/2009 | Rubbert et al. |
| 2010/0173259 A1 | 7/2010 | Vogel et al. |
| 2010/0185201 A1 | 7/2010 | Kim |
| 2010/0192375 A1 | 8/2010 | Jacquemyns |
| 2010/0196842 A1 | 8/2010 | Jacquemyns |
| 2011/0245951 A1 | 10/2011 | Gantes |
| 2011/0269104 A1 | 11/2011 | Berckmans, III et al. |
| 2012/0143364 A1 | 6/2012 | Mcleod et al. |
| 2012/0175799 A1 | 7/2012 | Karlsson et al. |
| 2012/0178045 A1 | 7/2012 | Massad |
| 2012/0270176 A1 | 10/2012 | Jacquemyns |
| 2012/0322025 A1 | 12/2012 | Ozawa et al. |
| 2013/0108988 A1 | 5/2013 | Simoncic |
| 2013/0108989 A1 | 5/2013 | Kim |
| 2013/0115573 A1 | 5/2013 | Lampl |
| 2013/0177864 A1 | 7/2013 | Hultgren et al. |
| 2013/0209953 A1 | 8/2013 | Arlinsky et al. |
| 2013/0224691 A1 | 8/2013 | Liechtung |
| 2013/0244208 A1 | 9/2013 | Rubbert |
| 2013/0277874 A1 | 10/2013 | Johnson et al. |
| 2013/0337412 A1 | 12/2013 | Kwon |
| 2014/0008826 A1 | 1/2014 | Dierkes et al. |
| 2014/0080093 A1 | 3/2014 | Rubbert |
| 2014/0113251 A1 | 4/2014 | Schweiger et al. |
| 2014/0193769 A1 | 7/2014 | Mackey |
| 2014/0193770 A1 | 7/2014 | Mackey |
| 2014/0193772 A1 | 7/2014 | Mackey |
| 2014/0205968 A1 | 7/2014 | Jung et al. |
| 2014/0215804 A1 | 8/2014 | Jacquemyns |
| 2014/0234804 A1 | 8/2014 | Huang et al. |
| 2014/0242541 A1 | 8/2014 | Jung et al. |
| 2014/0242547 A1 | 8/2014 | Randall |
| 2014/0248577 A1 | 9/2014 | Tahmasebi et al. |
| 2014/0255873 A1 | 9/2014 | Bullis et al. |
| 2014/0277665 A1 | 9/2014 | Fisker |
| 2014/0308623 A1 | 10/2014 | Chang |
| 2014/0315154 A1 | 10/2014 | Jung et al. |
| 2014/0316750 A1 | 10/2014 | Jung et al. |
| 2014/0358497 A1 | 12/2014 | Kuo et al. |
| 2015/0057675 A1 | 2/2015 | Akeel et al. |
| 2015/0150684 A1 | 6/2015 | De Clerck |
| 2015/0182301 A1 | 7/2015 | Hegland |
| 2015/0202028 A1 | 7/2015 | Randall |
| 2015/0216638 A1 | 8/2015 | Baaske et al. |
| 2015/0230894 A1 | 8/2015 | Juzbasic et al. |
| 2015/0250568 A1 | 9/2015 | Fisker et al. |
| 2015/0251405 A1 | 9/2015 | Kopelman et al. |
| 2015/0257853 A1 | 9/2015 | Jacquemyns |
| 2015/0282913 A1 | 10/2015 | Zegarelli |
| 2015/0289954 A1 | 10/2015 | Chang |
| 2015/0302170 A1 | 10/2015 | Berckmans, III et al. |
| 2015/0327967 A1 | 11/2015 | Baaske et al. |
| 2016/0000522 A1 | 1/2016 | Ripoche et al. |
| 2016/0008093 A1 | 1/2016 | Lampl |
| 2016/0030141 A1 | 2/2016 | Kopelman et al. |
| 2016/0074141 A1 | 3/2016 | Lozada |
| 2016/0143716 A1 | 5/2016 | Beyer et al. |
| 2016/0143717 A1 | 5/2016 | Samrano |
| 2016/0157970 A1 | 6/2016 | Gantes |
| 2016/0193019 A1 | 7/2016 | Heinz et al. |

FOREIGN PATENT DOCUMENTS

| | | |
|---|---|---|
| AU | 2002210903 B2 | 2/2006 |
| CN | 1678254 A | 10/2005 |
| DE | 4012327 A1 | 10/1991 |
| DE | 19947844 A1 | 4/2001 |
| DE | 102010031018 A1 | 1/2012 |
| EP | 1547544 A1 | 6/2005 |
| EP | 2272462 A1 | 1/2011 |
| EP | 2742906 A1 | 6/2014 |
| JP | 08-010268 | 1/1996 |
| JP | 3114270 U | 10/2005 |
| JP | 2007511275 A | 5/2007 |
| KR | 20030064772 | 8/2003 |
| KR | 20120053455 A | 5/2012 |
| KR | 20160018156 A | 2/2016 |
| KR | 20160018158 A | 2/2016 |
| KR | 20160056855 A | 5/2016 |
| SU | 1438757 A1 | 11/1988 |
| SU | 1674828 A1 | 9/1991 |
| WO | 9115163 A1 | 10/1991 |
| WO | 9627343 A1 | 9/1996 |
| WO | 3032131 A1 | 6/2000 |
| WO | 0234154 A2 | 5/2002 |
| WO | 2005055852 A2 | 6/2005 |
| WO | 2007104842 A1 | 9/2007 |
| WO | 2009000505 A1 | 12/2008 |
| WO | 2009048475 A1 | 4/2009 |
| WO | 2009073498 A1 | 6/2009 |
| WO | 2009089129 A1 | 7/2009 |
| WO | 2009094576 A1 | 7/2009 |
| WO | 2009105684 A1 | 8/2009 |
| WO | 2011003612 A1 | 1/2011 |
| WO | 2012006717 A1 | 1/2012 |
| WO | 2012076574 A2 | 6/2012 |
| WO | 2012085285 A2 | 6/2012 |
| WO | 2012110850 A2 | 8/2012 |
| WO | 2012162605 A2 | 11/2012 |
| WO | 2012163466 A1 | 12/2012 |
| WO | 2013026600 A1 | 2/2013 |
| WO | 2013181721 A2 | 12/2013 |
| WO | 2014135178 A1 | 9/2014 |
| WO | 2014138643 A2 | 9/2014 |
| WO | 2014198873 A1 | 12/2014 |

OTHER PUBLICATIONS

Russian Office Action for Application No. 2011136473 dated Feb. 22, 2014.

Mexican Office Action for Application No. MX/a/2011/008128 dated Apr. 9, 2014.

Japanese Office Action for Application No. 2011-546876 dated Aug. 5, 2014.

Extended European Search Report for Application No. 12790260.9 dated Jun. 19, 2015.

Australian Examination Report for Application No. 2010209671 dated Jan. 29, 2014.
Mexican Office Action for Application No. MX/a/2011/008128 dated Nov. 11, 2014.
Canadian Office Action for Application No. 2,750,698 dated Apr. 10, 2013.
International Search Report and Written Opinion for Application No. PCT/US2012/039569 dated Sep. 14, 2012.
P. Hahn, Fracture strengh of 3-unit inlay bridges after thermo-mechanical fatigue in a chewing simulator, http://www.gapless.de/, Oct. 25, 2001, 2 pages.
Chinese Office Action for Application No. 201080014124.5 dated Sep. 18, 2013.
Japanese Office Action for Application No. 2011-546876 dated Dec. 20, 2013.
Search Report for Russian Application No. 2014151779 dated Dec. 20, 2016.
Australian Examination Report for AU2017204455 dated Apr. 18, 2018.

* cited by examiner

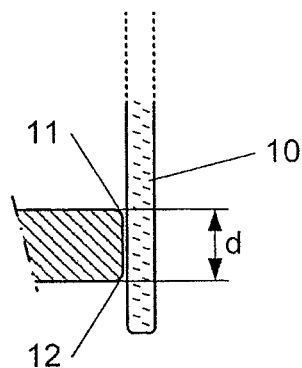
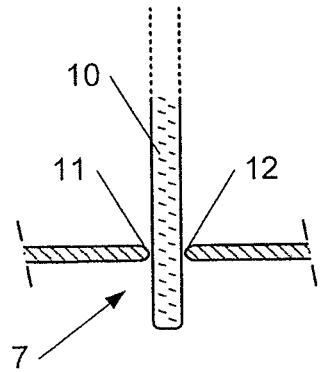
Fig. 3        Fig. 4
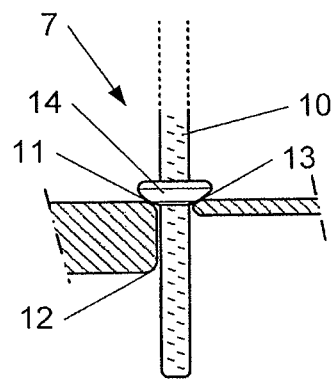
Fig. 5
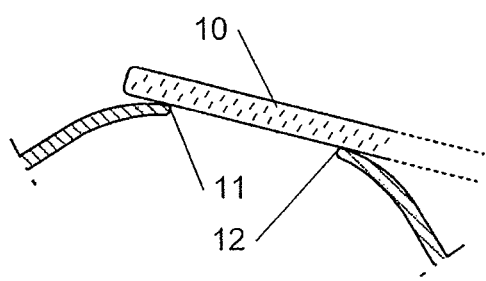
Fig. 6

METHOD OF PREPARATION FOR RESTORING TOOTH STRUCTURE

CROSS-REFERENCE TO RELATED APPLICATIONS

The present application is a continuation of U.S. patent application Ser. No. 12/698,777 filed Feb. 2, 2010, now U.S. Pat. No. 8,640,338, which is a continuation-in-part of U.S. patent application Ser. No. 12/364,216 filed Feb. 2, 2009, the disclosures of which are hereby incorporated herein by reference.

BACKGROUND OF THE INVENTION

The present invention concerns a method for producing a dentist tool formed by an overlay to be used by a dentist in removing tooth structure from a tooth, said method comprising the steps of:

determining a predetermined part of tooth structure to be removed so as to prepare said tooth for further treatment;

determining an overlay fitting said tooth and fitting at least a part of a neighboring tooth of said tooth;

simulating a movement to be followed by a dentist cutting tool in order to remove at least a part of said predetermined part;

determining a first guiding edge within said overlay, said first guiding edge corresponding to said movement so that it is provided to contact said dentist cutting tool following said movement, thereby being provided to guide said dentist cutting tool in a predetermined position, said first guiding edge being part of a guiding means;

producing said determined overlay with said guiding means.

The present invention further concerns a dentist tool to be used by a dentist in removing tooth structure from a tooth of a patient, which tooth is to be prepared for further treatment, said dentist tool comprising:

an overlay having a shape and dimensions so that it is releasably fixable over said tooth and being attachable to that tooth or to at least a part of a neighboring tooth of said tooth;

a first guiding edge within said overlay that is provided to contact a dentist cutting tool following a predetermined movement, said first guiding edge thereby being provided to guide said dentist cutting in a predetermined position.

When a patient needs a crown, bridge, onlay, inlay, veneer, or other restoring or other dental prosthesis and/or aesthetic tooth treatment, conventionally, during an initial office visit, the dentist identifies the needs of the patient and determines an appropriate treatment. During subsequent visits, in case the tooth comprises damaged and/or infected tooth structure, the dentist removes this tooth structure and reconstructs the tooth as much as possible using conventional techniques. Thereafter, the dentist performs the final preparation of the tooth for further treatment by removing tooth material, which is to be interpreted as original tooth structure and reconstructed tooth structure, with a dental cutting tool such as a high-speed drill. Relying upon eyesight and expertise, the dentist uses the drill to shape the tooth in a form that is suitable for further treatment, in particular a form onto which a crown, bridge, onlay, inlay, veneer or other tooth restoring part can be mounted. Then, the dentist takes an impression of the dental arch in which the prepared tooth is located, and sends the impression to the dental laboratory to have the dental technician make the restoration part. Using the impression of the prepared tooth, the dental technician produces a restoration part that matches the color, geometrical and material specifications, and sends it to the dentist. At the patient's final visit, the dentist adjusts the restoration part as necessary before fitting it in place.

A further dentist tool is disclosed in EP1547544. This dentist tool decreases the impact of the experience and expertise of the dentist onto the treatment, and it is used by a dentist in boring an artificial tooth root cavity. In EP1547544, guiding means, formed by a cylindrical hole, for guiding a drill in a straight-forward way, is provided. In such a manner an artificial tooth root cavity can be bored with greater precision even by a less experienced dentist. Moreover a suitable root cavity position can be calculated based on the information processed by the computer, so as to form in the most optimal way a cavity in the jaw bone.

A drawback of the known dentist tool is that it can only be used by a dentist in boring holes into the jaw bone. This dentist tool is not suitable to be used by a dentist in preparing a tooth for further treatment.

A further dentist tool is disclosed in DE4012327, which is considered close prior art. This dentist tool is formed by a template that comprises a guiding edge for guiding a dentist cutting tool along a predetermined movement. The guiding edge is provided at a predetermined height so that besides the position, also the depth of the dentist cutting tool can be guided. DE4012327 furthermore teaches how the dentist can use the template by placing the template in the mouth of the person and, using a moving-plate fixing the tilt of the dentist cutting tool into a predetermined inclination, running with the dentist cutting tool along the guiding edge thereby removing predetermined tooth structure.

A drawback of this known dentist tool is that the tilt is, because of the moving-plate, fixed in a predetermined inclination. Thereby, the dentist tool cannot guide a dentist cutting tool in a complex movement where also tilt variations occur. In particular when working with complex surfaces such as teeth, such complex movements are preferable.

BRIEF SUMMARY OF THE INVENTION

It is an object of the present invention to provide method for producing a dentist tool that is suitable for guiding a dentist cutting tool along a complex movement.

To this end, the method for producing a dentist tool according to the present invention is characterized in that said method comprises the further steps of:

determining a second guiding edge within said overlay that is spaced apart from said first guiding edge by a distance d of at least 0.5 mm, said second guiding edge corresponding to said movement so that it is provided to simultaneously with said first guiding edge contact said dentist cutting tool following said movement, said first and second guiding edge thereby being provided to guide said dentist cutting tool in a predetermined tilt, said second guiding edge being part of said guiding means.

The presence of the second guiding edge in the overlay results therein that the movement of a dentist cutting tool can be guided along a predetermined surface, whereas, in the prior art, the movement of the tool can only be guided along a predetermined line. Thereby also a guidance of the inclination of the dentist cutting tool can be obtained, which is not possible in the prior art. The presence of the second guiding edge results in that a dentist cutting tool can be guided along complex movements where position variations as well as tilt variations occur.

The determination of a predetermined part of tooth structure to be removed has the effect that this does not any more depend on the skills of the dentist. Determining and producing guiding edges into an overlay, which guiding edges are suitable for simultaneously contacting the dentist cutting tool, allows the cutting tool to be guided along a well determined path in an at least partially predetermined way. The overlay, having the guiding edges, accurately indicates onto the tooth the part to be removed from the tooth as determined by the computer. Moreover the tool according to the invention is provided to assist the dentist in removing tooth structure as the tool allows a dentist to remove at least part of a predetermined part of tooth structure.

It is to be noted that the term fitting is not to be interpreted in the narrow sense that the overlay should closely surround the teeth. It moreover should be interpreted as that an overlay should surround the teeth so as to be adequately in contact with the teeth and so that, once applied, it will not be released even if certain pressure, due to a normal use of the overlay, is applied.

Preferably, the method of this invention further comprises the steps of:

acquiring three-dimensional data relating to a shape of at least said tooth and at least said part of said neighboring tooth;

processing said three-dimensional data with a computer so as to determine significant dimensions and orientations for said overlay;

processing said three-dimensional data to determine said predetermined part.

Depending on the individual dental situation of a patient, the computer is programmed to determine an optimal way for shaping the tooth into a shape that is suitable for further treatment.

In a preferred embodiment of the invention, said first and said second guiding edge are designed for simultaneously contacting said dentist cutting tool at contacting points being longitudinally distanced from each other by said distance, said guiding edges thereby defining a guiding surface along which said dentist cutting tool is to be guided.

By simultaneously contacting two guiding edges with a cutting tool at contacting points being longitudinally distanced from each other, the cutting tool can be guided at least partially in a predetermined way. Preferably the cutting tool moves along the two guiding edges and thereby defines a guiding surface. This surface comprises the two guiding edges, and a cutting tool can be guided along this surface. This allows an accurate guiding in two dimensions.

Preferably, said guiding means comprise a guiding groove, which defines a path extending in a surface of said overlay and suitable for guiding said dentist cutting tool along said path in such a manner as to enable a guided removal of at least partially said predetermined part of tooth structure.

The two guiding edges, being distanced from each other, can be located one on the one side and the other on the other side of the path thereby defining the path between the two guiding edges. To this purpose, the distance between the two guiding edges should be substantially equal to a diameter of the cutting tool. Using the dentist cutting tool by simultaneously contacting the two guiding edges and following the path allows a guidance of the cutting tool at least in two dimensions. Considering a longitudinal cutting tool, the surface defined by the two guiding edges in this configuration will be substantially perpendicular to the direction of the cutting tool in use. The preferred tilt of the cutting tool, in this configuration, is perpendicular to the plane that is formed by the two guiding edges.

The two guiding edges, being distanced from each other, can also be both located on one side of the path. At least a third guiding edge will then define the other side of the path. Considering a longitudinal cutting tool in this configuration, the surface defined by the two guiding edges will be substantially parallel to the direction of the cutting tool in use. The third guiding edge in this configuration will provide a further guidance to the cutting tool thereby increasing the accuracy of the process of removal of tooth structure. Using the dentist tool by simultaneously contacting the two guiding edges and following the path in this configuration allows a guidance of the cutting tool in two dimensions and a guidance of inclination of the cutting tool.

Preferably, the method comprises the further steps of:

producing a tooth restoration part having an inner shape determined so as to fit a predetermined remaining part of tooth structure of said tooth, and having an outer shape determined so as to fit together with remaining neighboring teeth.

An advantage of the method according to the invention is that the shape of the remaining part of tooth structure of the prepared tooth is known in advance due to the guided removal of tooth structure. This improves further treatment, such as preparing a temporary or final inlay, onlay, bridge, crown or veneer in advance based on the three-dimensional data. This results in that less office visits are required, as the dentist can both prepare the tooth and mount the tooth restoration part onto the prepared tooth in one single visit. This way of working does not only save time and thus costs, also the inconvenience for the patient is strongly decreased. Furthermore the chances that a prepared tooth gets contaminated, and the resulting complications, are reduced to a minimum.

Preferably, the method comprises the further steps of:

processing said three-dimensional data to simulate a tooth restoration part having an inner shape determined so as to fit a predetermined remaining part of tooth structure of said tooth, and having an outer shape determined so as to fit together with remaining neighboring teeth;

producing said tooth restoration part.

Thereby, an individually designed tooth restoration part can be delivered together with the dentist tool according to the invention. This is possible because the final shape of the prepared tooth, when using the dentist tool, is known in advance. The result is that less dental visits are required to place a restoration part.

Preferably, said predetermined part is determined by:

firstly determining an outer shape of said tooth restoration part so is that it fits together with remaining neighboring teeth, and determining an inner shape of said tooth restoration part that is compatible with said outer shape;

secondly determining a shape of remaining tooth structure so that said tooth restoration part having said inner shape fits said shape of remaining tooth structure;

thirdly determining said predetermined part as being the part of tooth structure to be removed so as to have said shape of remaining tooth structure left.

Starting with determining a tooth restoration part instead of, as conventionally, preparing the tooth, has an advantage. A tooth restoration part can be determined having an outer shape so as to optimally fit together with remaining neighboring teeth. Procedures for determination of such an outer shape are known to the person skilled in the art. An inner shape is then determined, which inner shape is compatible with said outer shape. Criteria for being compatible depend on the material that is to be used and mainly concern strength parameters, production parameters and parameters relating to the mounting of the restoration part onto the tooth and/or teeth. Preferably the inner shape is determined in such a manner that a minimum amount of material is required to produce the tooth restoration part. This at its turn results in that the remaining tooth structure, required to fit to this inner shape, is as large as possible, namely, the more material of a restored tooth is tooth restoration material, the less material of that restored tooth is tooth structure. Then the predetermined part can be determined as being the part of tooth structure to be removed so as to have said shape of remaining tooth structure left. Thus first determining the tooth restoration part, results in that a minimum of tooth structure is to be removed from the tooth and maximum conservation of the original tooth structure. As it is best to maintain as much of the original tooth structure, this is an advantage.

Providing the determined tooth restoration part having the determined outer and inner shape together with the dental tool, results in that less office visits are required because the dentist can prepare the tooth and mount the tooth restoration part onto the prepared tooth in one single visit.

Preferably said dentist tool comprises at least one further overlay, said overlay and said at least one further overlay being determined to guide a dentist tool in removing tooth structure in a plurality of stages, in which said guiding means in said overlay is provided to guide said cutting tool in one of said plurality of stages, and at least one further guiding means in said at least one further overlay is provided to guide said cutting tool in at least one further of said plurality of stages, the method further comprising the steps of:

determining at least one further overlay fitting said tooth and fitting at least a part of said neighboring tooth;

simulating at least one further movement to be followed by said dentist cutting tool in order to remove at least one further part of said predetermined part;

determining at least one further first guiding edge within said at least one further overlay, said at least one further first guiding edge corresponding to said at least one further movement so that it is provided to contact said dentist cutting tool following said at least one further movement, thereby being provided to guide said dentist cutting tool in a predetermined position, said at least one further first guiding edge being part of said at least one further guiding means;

determining at least one further second guiding edge within said at least one further overlay that is spaced apart from said at least one further first guiding edge by a distance d of at least 0.5 mm, said at least one further second guiding edge corresponding to said at least one further movement so that it is provided to simultaneously with said at least one further first guiding edge contact said dentist cutting tool following said at least one further movement, said at least one further first and second guiding edge thereby being provided to guide said dentist cutting tool in a predetermined tilt, said at least one further second guiding edge being part of said at least one further guiding means producing said at least one further overlay with said at least one further guiding means.

Producing a plurality of overlays instead of just one overlay provides a further flexibility in the method for producing the dentist tool. Different overlays can be provided for guiding a dentist cutting tool along different sides of the tooth to be prepared, so that for example a circumferential path can be defined by using multiple overlays each defining a different segment of the circumferential path. Multiple overlays furthermore allow to use different dental cutting tools, which is necessary in some cases. Different overlays can be provided for preparing a tooth in multiple stages, in which for example a first stage is provided to smoothen the upper part of the tooth, a second and a third stage are provided to cut away the longitudinal and transversal sides of the tooth, and a fourth and fifth stage are provided to round off the edges between the longitudinal and transversal sides each at a different side of the tooth. Preparing a tooth in stages allows each overlay to be designed having guiding edges which are particularly determined for guiding the cutting tool in a particular way characterized by the particular stage.

BRIEF DESCRIPTION OF THE DRAWINGS

The invention will now be described in more details with respect to the drawings illustrating some preferred embodiments of the invention. In the drawings:

FIG. 3 shows a cross section of part of an overlay with guiding means according to one embodiment of the invention and a cutting tool;

FIG. 4 shows a cross section of part of an overlay with guiding means according to another embodiment of the invention and a cutting tool;

FIG. 5 shows a cross section of part of an overlay with guiding means according to the invention and a cutting tool;

FIG. 6 shows a cross section of part of an overlay with guiding means according to a further embodiment of the invention and a cutting tool;

FIG. 8 shows a cross-section of the overlay shown in FIG. 7a.

In the drawings a same reference number has been allocated to a same or analogous element.

DETAILED DESCRIPTION

Figure 1:
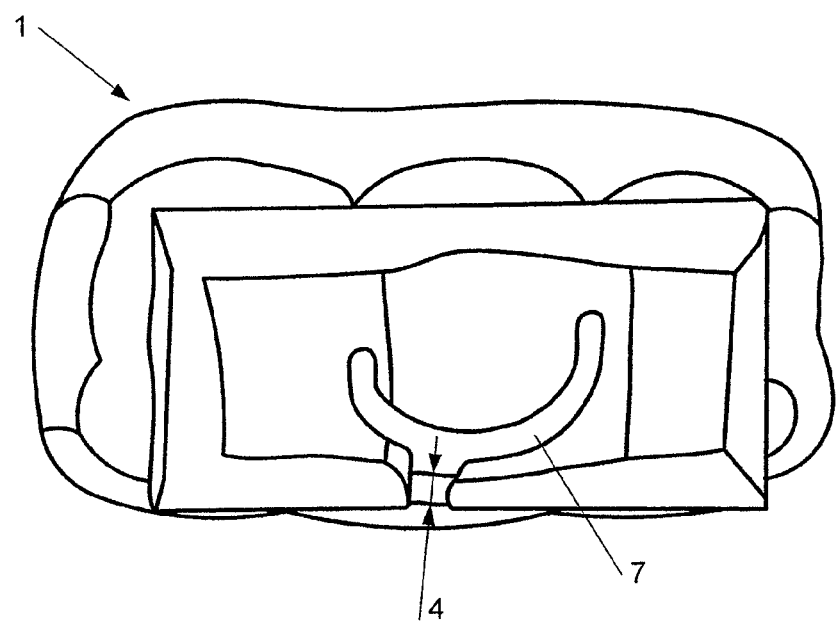
FIG. 1 shows a top view of an overlay with a guiding groove according to the invention.

The terms "lower", "upper" etc. and derived directional terms such as "horizontal" and "vertical" are based on a normal configuration of an overlay as shown in the drawings, wherein the overlay fits onto teeth with their root extending vertically downward. The term dentist in this text is not to be interpreted restrictive and can also be read as dental technician, dental assistant, dental auxiliary, dental therapist, dental designer etc.

Figure 2:
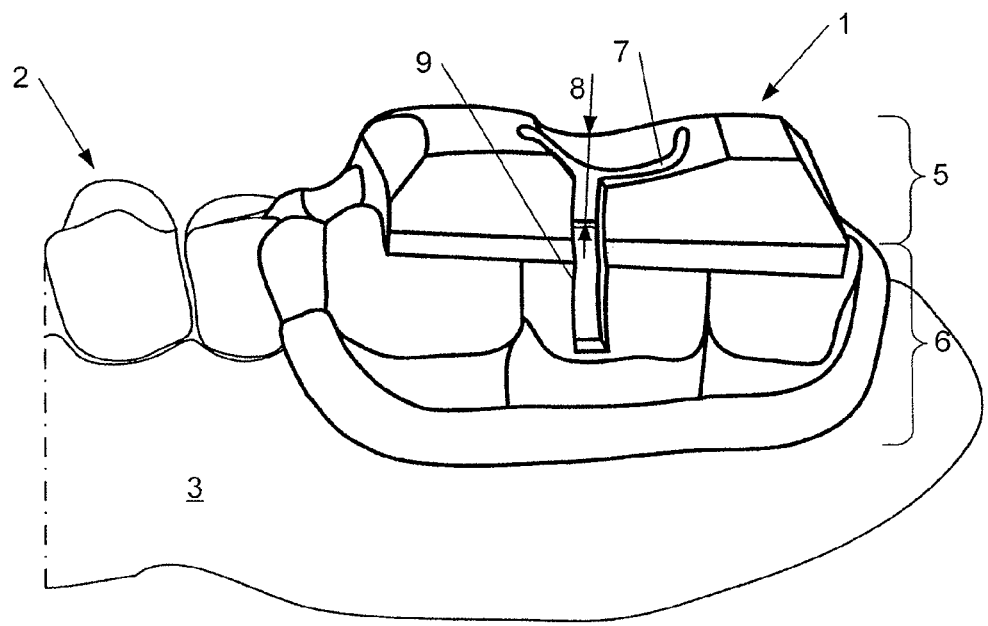
FIG. 2 shows a side view of an overlay with a guiding groove placed onto a patient's teeth.
Figure 7A:
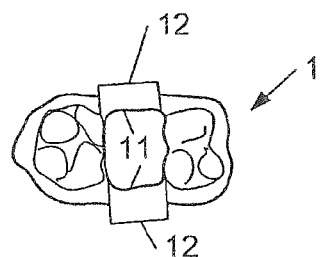
FIGS. 7A-E shows various stages for the removal of tooth structure for preparing a tooth for mounting a crown or a bridge.

The invention provides a method for producing a dentist tool formed by an overlay 1 to be used by a dentist in removing tooth structure. Furthermore, the invention provides an overlay 1 obtainable by this method. FIGS. 1 and 2 show such an overlay 1 arranged onto the teeth 2 of a patient. Preferably, the invention provides a method for producing the dentist tool and a tooth restoration part in such a manner that the tooth restoration part will fit the tooth that is prepared using the dentist tool.

The dentist tool according to the invention is preferably used by a dentist in preparing a tooth for a restoration such as placing inlays and onlays, crowns, bridges, and veneers. Such restoration requires a restoration part to be produced in order to fit the tooth after the latter has been prepared. Using the dentist tool according to the invention results in that the shape of the prepared tooth, which conventionally is only known after preparation, is determined in advance. Based on this knowledge, a restoration part can be produced in advance so that this restoration part is available to the dentist even before he or she starts preparing the tooth, and can be mounted directly after preparation of the tooth. This results in that the patient suffers less inconvenience, in particular that the number of visits to the dentist are reduced. Furthermore the chances that a prepared tooth gets contaminated, and the resulting complications, are reduced to a minimum.

Preferably, preparing a tooth for further treatment is performed onto a substantially healthy tooth. When a tooth is damaged or infected, the damaged and/or infected parts of the tooth will have to be removed first, and the tooth will have to be reconstructed before preparing the tooth for further treatment. This minimizes the chance that an infection develops underneath a tooth restoration part. This also maximizes the lifetime of the tooth restoration part as the basis for the tooth restoration part, namely the tooth, does not contain damaged parts any more.

It may be possible to utilize an overlay made for one tooth in the preparation of a tooth of another patient, where such other patient's tooth has sufficiently similar dimensions and shape. Therefore, it is within the scope of this invention to have prepared some overlays which can be standardized, reused and/or reproduced. Also, it is within the scope of this invention to utilize data obtained in the preparation of prior overlays and restoration parts in the design and generation of new overlays having substantially similar dimensions and shapes.

Several methods are known for acquiring three-dimensional data from a patient's dentition. Such data can be retrieved, for example by processing photographs taken from the patient's dentition. Another method is making a physical impression of the dentition and then subsequently scanning this impression or a reversed cast of the impression. Such scanning can be conducted with a CAD/CAM 3D scanning device. Illustrative of such a device is the FreeForm® from SensAble Technologies Inc. of Woburn, Mass., USA. While such a scanning device can scan a model of the dental arch with a tolerance of about 10 μm this does not take into account other error factors obtained from the making of the impression and the casting of the dental impression. In preparing the ultimate restoration part or dental prosthesis, these other error factors or tolerances must be considered.

The CAD program chooses the specific configuration for the overlay, sometimes referred to as reduction trays, and ultimately the configuration for the prepared tooth by utilizing certain protocols which are based on prior experience for preparing dental prostheses.

In one embodiment of the invention, the digital file for the subject tooth can be compared with an existing database for such prostheses. Such an illustrative database is available from Heraeus Kulzer Tooth Library of Heraeus Kulzer GmbH of Hanau Germany. This data base has also been integrated into the SensAble Dental Lab System (SDLS). A prosthesis (e.g. a crown or onlay) comparable to that appropriate for the subject tooth is chosen from the Kulzer database. That prosthesis information includes the configuration and dimensions for the prepared tooth, which would correspond to the internal surface of the prosthesis. This internal configuration in the Kulzer database for that prepared crown is utilized to design the overlays (reduction trays) for use in the preparation of the patient's tooth. In the design of the overlays, fundamental principles and objectives known in the art are utilized, for example to remove the minimum amount of original tooth surface.

For example, in a set of overlays or reduction trays, there may be one overlay or tray for reduction of the medial and distal surface (front and back) and another tray for the occlusive (top) surface. Also, there could be two finishing trays which cut lingual (tongue) surface and buccal (cheek) surface of the tooth. For preparation for a crown, one would need additional trays for gingival margins.

The foregoing describes a typical use of the method but a greater or fewer number of reduction trays or overlays may be appropriate to carry out the preparation of the tooth for later installation of the dental prosthesis or restoration part. After acquiring the three-dimensional data of the tooth, this data gets processed by a computer so as to determine an overlay 1 fitting the teeth 2 of the patient. To this end, the inner shape of the overlay preferably corresponds to the outer shape of the tooth to be prepared and to the outer shape of at least part of a neighboring tooth. Overlay should fit the teeth in such a manner that once the overlay is placed onto the teeth, it will only come off by applying a sufficiently high force to the overlay. During preparation of the tooth, small forces may be applied to the overlay, which preferably should not modify the position of the overlay on the teeth. Preferably, the overlay 1 extends over the teeth 2 so as to also cover part of the gingiva 3 or of neighboring teeth for stability purpose and protection purpose. As the dentist will use the overlay 1 for removing tooth material, it is advantageous that the overlay 1 is located onto the tooth in a stable way. As an example, an overlay 1 closely fitting the tooth, two neighboring teeth, and part of the gingiva 3, ensures that a dentist can arrange and maintain the overlay in a stable position during removal of tooth structure. When the overlay 1 covers a part of the gingiva 3, at least this part of the gingiva 3 will be protected during the process of removing tooth structure.

It is to be noted that an overlay 1 according to the invention can cover multiple teeth at once and can be provided to be used by a dentist in preparing a plurality of teeth using one single overlay 1. This can be advantageous in the process of preparing teeth for placing veneers. Such an overlay comprises guiding means, as will be explained further, for each tooth that needs to be prepared.

The determined overlay 1 has a thickness 4 that mainly depends on the required strength thereof, and thus also the material it will be made of. An overlay 1 according to the invention can have a constant overall thickness 4. A substantially constant overall thickness is preferred for an overlay to be used by a dentist in preparing a tooth or teeth for placing veneers. An overlay to be used for preparing a tooth for placing a bridge or a crown preferably comprises an upper, guiding part 5, and a lower, supporting part 6. The supporting part 6 of the overlay 1 will ensure that the overlay 1 can be arranged in a stable way onto the teeth 2, whereas the guiding part 5 of the overlay 1 will guide the dentist cutting tool and preferably will also determine the maximal penetration depth of the cutting tool in the tooth. To this end, the thickness of the guiding part 5 of the overlay 1 will preferably be determined case by case together with the determination of the guiding means 7, as will be explained further. The thickness 4 of the supporting part 6 of the overlay 1 can be more freely chosen depending on the preferences of the dentist and/or the programmation of the computer.

After acquiring the three-dimensional data, this data gets also processed by a computer so as to determine a predetermined part of tooth structure to be removed from the tooth by the dentist. The predetermined part will be determined in view of the further treatment. If a particular shape of the prepared tooth is required for allowing further treatment, the predetermined part will be chosen so that after preparation of the tooth, this particular shape will remain.

Determining the predetermined part depends on many parameters and will differ from case to case. Parameters are the location of the tooth in the mouth of the patient, amount and location of the damaged tooth structure, distance of the tooth to neighboring teeth, etc. In a preferred embodiment, the computer will also take into account the different parts of the tooth such as the enamel, dentin, pulp, cementum, etc. in determining the predetermined part. It is also understood within the general aspects of the invention that the patient's tooth may have to be built up through conventional techniques and materials prior to the actual step of preparation of the tooth, utilizing the overlay.

According to the invention, the computer is programmed to determine the predetermined part of tooth structure to be removed without assistance of a dentist except for what concerns the input of the initial data of the tooth. However also according to the invention, the computer can be programmed to determine the predetermined part in cooperation with a dentist, where, for example, the dentist decides on some parameters. This cooperation can be established by visualizing data relating to the tooth onto a computer display and allowing the dentist at least to enter one parameter relating to the preparation of the tooth. Preferably a preview of the tooth is visualized onto the computer display together with a preview of a simulation of the prepared tooth, so as to allow a dentist to see the impact of chosen parameters onto the prepared tooth. The latter feature provides a larger degree of freedom to the dentist and allows a less experienced dentist to consult a more experienced dentist about a case, based on the data in the computer. In this manner, the method for producing a dentist tool according to the invention allows a less experienced dentist to decide on a further treatment and prepare a tooth for further treatment with a same quality as if he or she was an experienced dentist.

In another embodiment, the computer is programmed to determine the predetermined part of tooth structure to be removed in several phases. At the end of each phase, the computer proposes a simulated solution to the dentist and requests for approval or correction of the proposed solution.

Preferably the predetermined part will be determined in several steps. In a first step, the outer shape of the tooth restoring part is to be determined so that the tooth restoring part fits with the remaining teeth and fits into the dental arch of the patient. A bite lift or other corrective amendment can be directly integrated into the design of the outer shape. Then, based on this determined outer shape, an inner shape gets determined that is compatible with the outer shape. In such a manner, a tooth restoration part can be determined having an optimal outer shape, and an optimal construction in the sense that it is strong enough and a minimum of material is needed. In a following step, the shape of remaining tooth structure is to be determined so that the inner shape of the tooth restoring part fits the remaining tooth structure after removal of tooth structure. In a final step, the predetermined part of tooth structure is determined as the part of tooth structure to be removed to have the shape of remaining tooth structure left. This way of working allows determining the outer shape of the tooth restoring part using best fit programs. Conventionally, the dentist will not follow the steps in the succession as mentioned above. The dentist will work the other way around, as the dentist will need to know the shape of the prepared tooth to determine the inner shape of the restoration part, after which the dentist will determine an appropriate outer shape. Firstly determining the tooth restoration part, according to a preferred embodiment of the invention, results in that a minimum of tooth structure is to be removed from the tooth and a maximum conservation of the original tooth structure can be obtained.

Once the predetermined part has been determined, guiding means can be determined. The purpose of the guiding means is to guide a dentist cutting tool, i.e. a drill, along a simulated movement whereby the cutting tool removes at least a part of the predetermined part. To this end, it will be understood that in some cases, the dimensions of the dentist cutting tool, such as the length, diameter, cross-sectional form, etc. will be determining for which movement is to be made with the cutting tool to remove a certain part of tooth structure. It will also be understood that in many cases, it will not be sufficient to make one single movement for removing all the predetermined part. Via computer calculation and/or simulation, one or more movements can be simulated for removing the predetermined part of tooth structure. It is to be understood that a movement in this context does not only relates to a two-dimensional position, but relates to the movement of the cutting tool in all its aspects such as horizontal movement, vertical movement and tilt movement.

The guiding means according to the invention comprise at least two guiding edges 11, 12 (FIGS. 3-6). Two of these guiding edges 11, 12 are spaced apart from each other with a distance d of at least 0.5 mm. The guiding edges 11, 12 are provided to simultaneously contact the cutting tool 10 thereby guiding the cutting tool 10 at least partially into a predetermined movement. It is to be understood in this context that a surface having a length and having a width which are at least 0.5 mm can be considered as the said at least two guiding edges 11, 12. Namely, the two outer edges of the surface are provided to simultaneously contact the cutting tool 10, and are spaced apart with a distance d of at least 0.5 mm.

The guiding edges 11, 12 are determined in correspondence with the simulated movement of the dentist cutting tool such that both guiding edges 11 and 12 are simultaneously in contact with the cutting tool following the movement. Preferably, the guiding edges are simultaneously and constantly in contact with the cutting tool, preferably during the whole of the movement. The contact between a guiding edge and the cutting tool, along the movement, is preferably a point of contact.

Preferably the two guiding edges 11, 12 are spaced apart from each other with a distance d of at least 1 mm, more preferably of at least 2 mm and most preferably of at least 3 mm. Increasing the distance d between the two edges 11, 12 will increase the guiding quality as it will be much easier for a dentist to control the cutting tool 10 onto larger guiding means.

The guiding edges 11, 12 are provided in such a manner as to be simultaneously contacted by the cutting tool at two contacting points. As illustrated in FIG. 3, preferably these contacting points 11, 12, considered on the cutting tool 10, are longitudinally spaced apart by the distance d. When the cutting tool 10 is arranged substantially perpendicular to the guiding edges, the distance between the contacting points will be substantially the same as the distance d between the guiding edges. FIG. 3 illustrates a cutting tool 10 lying simultaneously against the two guiding edges 11, 12. The guiding edges 11, 12 in this configuration define a surface along which the cutting tool 10 can be guided.

However the guiding edges 11, 12 can also simultaneously contact the cutting tool 10 at two contacting points being located each at one side of the cutting tool 10, as illustrated in FIG. 4. In this configuration, the guiding edges 11, 12 define a guiding groove in which the cutting tool can be guided. The guiding groove 7 is preferably determined so as to define a path laying in the upper surface of the overlay 1. The groove 7 is provided for guiding a dentist cutting tool along this path, and to this end, the groove 7 extends through the overlay so as to form a communication between the inside of the overlay and the outer environment. When more than one path is to be followed for removing the predetermined part, multiple guiding grooves 7 will have to be determined.

A combination of these two mentioned configurations is illustrated in FIG. 5. In this figure, a first and second guiding edge 11, 12, being the two guiding edges that are spaced apart, can be seen on the left hand side, which edges define a guiding surface. A third guiding edge 13 can be seen on the right hand side, which edge defines, together with the first and second guiding edge 11, 12, a path. This configuration therefore allows a cutting tool to be guided into both a horizontal movement and a tilt.

As can be seen in FIG. 5, the cutting tool 10 preferably comprises a collar 14 mounted onto the cutting tool 10. Preferably at least one of the guiding edges 11, 12, 13 is provided to guide the collar 14 of the cutting tool 10 thereby guiding the cutting tool 10 into a predetermined vertical position or height or depth. As can be seen in the FIG. 5, the guiding groove 7 defining a horizontal path, furthermore defines a predetermined height 8 for each horizontal location of the cutting tool, so as to guide the cutting tool 10 along a horizontal path and in a predetermined tilt, and also guiding the cutting tool in the vertical way.

FIG. 6 illustrates a variant on the embodiment shown in FIG. 3, and shows the guiding edges 11, 12, which are provided to simultaneously contact the cutting tool at two contacting points being longitudinally distanced from each other. In this embodiment, tooth structure can be removed that is located in between the two guiding edges 11, 12. In particular in preparing a tooth for placing veneers, this embodiment will be used.

For mounting a crown or a bridge, the tooth is to be shaped into a truncated pyramid having rounded edges. To this end the outer and upper part of the tooth are to be removed. This removal of tooth structure can be guided by the dentist tool according to the invention.

Figure 8:
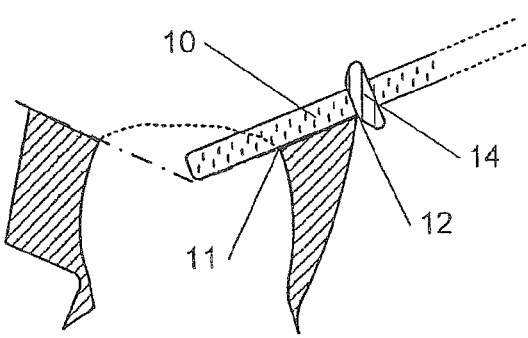

Preferably the removal of tooth structure for preparing a tooth for mounting a crown or a bridge is performed in several stages shown in FIG. 7. In a first stage, shown in FIG. 7a and FIG. 8, the upper part of the tooth gets smoothened. This can be done using an overlay having guiding edges 11, 12 as illustrated in FIG. 6. However in practice, it is preferred that the upper part gets shaped into a V-form. To this end, the upper part preferably gets smoothened using two guiding means as illustrated in FIG. 3, which guiding means are located on both sides of the tooth in such a manner that said guiding means are provided guide said cutting tool to cut said upper part into a V-shape.

Figure 7B:
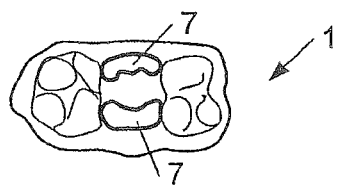
Figure 7C:
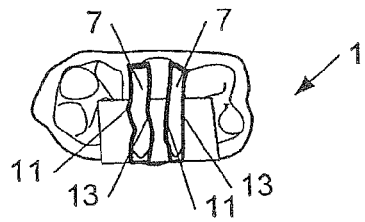

In a second and a third stage, shown in FIGS. 7b and 7c, the longitudinal and transversal sides of the tooth get cut, so as to obtain a truncated pyramid form. The cutting of these sides can be guided by overlays having guiding means as illustrated in FIGS. 3, 4 or preferably FIG. 5. Preferably one overlay comprises two such guiding means each defining a path extending in the surface of the overlay, the paths extending parallel to each other, each on one side of the tooth.

Figure 7D:
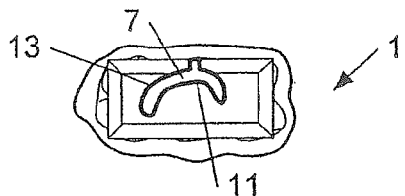
Figure 7E:
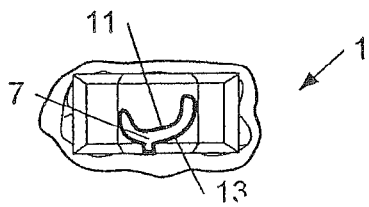

In a fourth and fifth stage, shown in FIGS. 7d and 7e, the edges of the pyramid get rounded. Rounding these edges can be guided by an overlay as shown in FIGS. 1 and 2. Such an overlay comprises a path extending in the surface of the overlay and defining a segment of a circle. Each side of the path is defined by a guiding surface having at least two guiding edges, as illustrated in FIG. 3. The height of the guiding part 5 of the overlay 1 is defined so as to guide the cutting tool 10 in a predetermined vertical position.

In this succession of stages, the first stage could be executed as the last stage instead of as the first. However tests have shown that starting with smoothening the upper part of the tooth is advantageous in the process of preparing the tooth.

Once the overlay 1 and the guiding means are determined, the determined overlay 1 having the determined guiding means can be produced. This can be done by any known means such as a CAD/CAM system, rapid prototyping or 3D printing. When multiple guiding means have been determined, multiple overlays 1 can be produced each comprising one or several guiding means. Preferably, a rapid prototyping apparatus creates the overlay with a tolerance of about 30 μm.

The overlay 1 has, as already mentioned above, a lower, supporting part 6 and an upper, guiding part 5. As can be seen in the figures, the guiding part 5 has a certain thickness 8, which defines the height 8 of the path and enables the cutting tool to be guided in the vertical way. Preferably the supporting part 6 and/or guiding part 5 comprises a vertical opening 9 from the side to the guiding groove 7, provided to serve as an entrance into the guiding groove 7 for a dental cutting tool. In particular when a cutting tool has a tip portion that has a diameter that is larger than the diameter of the main portion of the cutting tool, for example a high-speed drill with a tip in the form of a ball, this opening is advantageous. Entering such a cutting tool into the guiding groove 7 via the upper part of the overlay would at least partially widen the guiding groove 7 thereby at least partially taking away its possibility to firmly guide the cutting tool along the predetermined path. Furthermore a side entrance 9 is preferred over an entrance via the upper part as it will be easier to enter the cutting tool in a controlled manner into the guiding groove 7.

When a guiding groove 7 is determined to form a circular path in the horizontal plane, it will be preferred to split up this path into several segments, and produce multiple overlays 1 each having a guiding groove 7 corresponding to one segment of this path. This will result in a set of overlays 1 which can be used by a dentist one after the other to remove tooth structure following this circular path. Each overlay 1 of the set of overlays 1 will guide the cutting tool along a particular side of the tooth.

In the embodiment where the predetermined part is not determined based on the shape of the tooth restoration part, the latter can be determined based on the data in the computer. Outer shape of the tooth restoration part can be determined in several ways, all known to the person skilled in the art. A bite lift or other corrective amendment can be directly integrated into the design of the outer shape. A first possibility is to shape the tooth restoration part so that it resembles the outer shape of the original tooth. A second possibility is to shape the tooth restoration part so that it fits with neighboring teeth. A third possibility is a combination of the first and second, and modifies the shape of the original tooth to better fit with the neighboring teeth. Inner shape of the tooth restoration part will be determined based on the simulation of the preparation of the tooth. As the tooth will be prepared in a guided manner, it is known in advance what the shape will be of the prepared tooth. The inner shape of the tooth restoration part will be chosen so that it fits the shape of the prepared tooth.

Preferably the method according to the invention further comprises the step of producing a tooth restoration part.

Similar to the determination of the predetermined part, a tooth restoration part can be determined by a computer without any interaction of a dentist. However it will be preferred that the computer determines the tooth restoration part in cooperation with a dentist, for example in a way as described above. The computer can, in this process of determining a tooth restoration part, perform predetermined clinical checks and alert the dentist in case the tooth restoration part does not meet the standard norms. This will enable a dentist to design a tooth restoration part in a fast and reliable manner.

The production of the tooth restoration part can be done by any means known to the skilled person such as a CAD/CAM system.

The invention claimed is:

1. A method for producing a dentist tool comprising an overlay to be used by a dentist with at least one dentist cutting tool in removing tooth structure from a working tooth, the method comprising:

simulating any one of any combination of predetermined horizontal, vertical, and tilt movements to be followed by at least one dentist cutting tool in order to remove at least a portion of a predetermined part of tooth structure of the working tooth so as to prepare the working tooth for treatment;

determining an overlay with a surface configured for fitting either of or both the working tooth and a neighboring tooth of the working tooth such that the surface, when so fitted, contacts the respective one or ones of the working tooth and the neighboring tooth of the working tooth to maintain the overlay releasably fixed in a same position over the working tooth during movement of the dentist cutting tool along first and second guiding edges of the overlay, wherein the determining comprises:

i) determining the first guiding edge within the overlay, the first guiding edge corresponding to the respective one or combination of the predetermined horizontal, vertical, and tilt movements simulated; and ii) determining the second guiding edge within the overlay that is spaced apart from the first guiding edge by a distance (d), whereby the second guiding edge corresponds to the at least one of the predetermined horizontal, vertical, and tilt movements simulated, the first and second guiding edges thereby being provided to contact the dentist cutting tool so as to guide the dentist cutting tool such that the dentist cutting tool follows the at least one predetermined horizontal, vertical, and tilt movements for removal of at least a portion of the predetermined part of tooth structure of the working tooth to be removed; and producing the determined overlay with the first and the second guiding edges, the produced overlay having the determined surface configured for fitting the respective one or ones of the working tooth and the neighboring tooth of the working tooth such that the determined surface of the produced overlay, when so fitted, contacts the respective one or ones of the working tooth and the neighboring tooth of the working tooth to maintain the overlay releasably fixed in the same position over the working tooth during movement of the dental cutting tool along the first and the second guiding edges, wherein the surface of the determined and produced overlay is configured to extend between and to contact respective top and bottom portions of the one or ones of the working tooth and the neighboring tooth of the working tooth, the respective bottom portion or portions being adjacent to a gingiva of the patient.

2. A method of preparation for restoring tooth structure, the method comprising:

the method of claim 1;

producing a predetermined tooth restoration part having an inner shape that fits the working tooth after the removal of the predetermined part of the tooth structure to be removed from the working tooth; and placing the predetermined tooth restoration part on remaining tooth structure of the working tooth after the removal of the predetermined part of the tooth structure to be removed from the working tooth.

3. The method of claim 2, further comprising:

determining the predetermined part of the tooth structure to be removed from the working tooth so as to prepare the working tooth for treatment; and processing acquired three-dimensional data with a suitable computer program to convert the acquired three-dimensional data relating to a shape of at least the working tooth data into processed three-dimensional data defining the determined overlay with the determined first and the determined second guiding edges and for fitting the working tooth.

4. The method of claim 2, further comprising:

determining the overlay so as to also fit at least the part of the neighboring tooth of the working tooth when the determined overlay is configured for fitting the working tooth;

determining the predetermined part of the tooth structure to be removed from the working tooth so as to prepare the working tooth for treatment; and processing acquired three-dimensional data relating to a shape of the part or parts of the working tooth and the neighboring tooth with a suitable computer program to convert the acquired three-dimensional data into processed three-dimensional data defining the overlay with the first and the second guiding edges within the overlay and for fitting the part or parts of the working tooth and the neighboring tooth.

5. The method of claim 2, further comprising:

processing the acquired three-dimensional data to simulate the tooth restoration part having an inner shape determined so as to fit the remaining tooth structure of the working tooth after the removal of the predetermined part of the tooth structure to be removed from the working tooth and having an outer shape determined so as to correspond with a remaining neighboring tooth of the working tooth, wherein the remaining tooth structure of the working tooth after the removal of the predetermined part of the tooth structure to be removed from the working tooth and the tooth restoration part are determined by:

determining an outer shape of the tooth restoration part so as to correspond with the remaining neighboring tooth;

determining an inner shape of the tooth restoration part so as to be compatible with the outer shape;

determining a shape of remaining tooth structure of the working tooth after the removal of the predetermined part of the tooth structure to be removed so that the tooth restoration part having the inner shape fits the remaining tooth structure of the working tooth after the removal of the predetermined part of the tooth structure to be removed from the working tooth; and determining the predetermined part of the tooth structure of the tooth to be removed so as to determine the shape of remaining tooth structure of the working tooth existing after the removal of the predetermined part of the tooth structure to be removed from the working tooth.

6. A method of preparation for restoring tooth structure, the method comprising:

the method of claim 1; and producing a tooth restoration part having an inner shape determined so as to fit remaining tooth structure of the working tooth after the removal of the predetermined part of the tooth structure to be removed from the working tooth and having an outer shape based on geometric specifications of the working tooth and the neighboring tooth of the working tooth prior to the removal of the predetermined part of the tooth structure to be removed from the working tooth so as to correspond the tooth restoration part with the neighboring tooth.

7. The method of claim 6, the method further comprising:

processing acquired three-dimensional data relating to a shape of at least the working tooth and the neighboring tooth of the working tooth with a suitable computer program to convert the acquired three-dimensional data into processed three-dimensional data defining the determined overlay with the determined first and the determined second guiding edges and for fitting the respective one or both of the working tooth and the neighboring tooth; and processing the acquired three-dimensional data to simulate the tooth restoration part.

8. The method of claim 6, wherein the predetermined part of the tooth structure to be removed from the working tooth and the tooth restoration part are determined by:

determining an outer shape of the tooth restoration part so as to correspond to a shape of the neighboring tooth of the working tooth;

determining a shape of remaining tooth structure of the working tooth existing after removal of the predetermined part of the tooth structure to be removed from the working tooth so that the inner shape of the tooth restoration part can be determined to fit over the predetermined remaining tooth structure of the working tooth; and determining the inner shape of the tooth restoration part so as to be compatible with the outer shape of the tooth restoration part and by determining a shape that fits over the predetermined remaining tooth structure of the working tooth after the removal of the predetermined part of the tooth structure to be removed from the working tooth.

9. The method of claim 1, further comprising:

processing three-dimensional data relating to a shape of at least the working tooth with a suitable computer program to convert the three-dimensional data into processed three-dimensional data defining the determined overlay with the determined first and the determined second guiding edges within the overlay and for fitting the working tooth.

10. The method of claim 9, further comprising:

determining the predetermined part of the tooth structure to be removed from the working tooth so as to prepare the working tooth for treatment.

11. The method of claim 1, further comprising:

determining the overlay so as to also fit at least a fitted part of the neighboring tooth of the working tooth when the determined overlay is configured for fitting the working tooth;

processing three-dimensional data relating to a shape of at least the working tooth and at least the fitted part of the neighboring tooth with a suitable computer program to convert the three-dimensional data into processed three-dimensional data defining the determined overlay with the determined first and the determined second guiding edges and for fitting the working tooth and the part of the neighboring tooth.

12. The method of claim 11, further comprising:

determining the predetermined part of the tooth structure to be removed from the working tooth so as to prepare the working tooth for treatment.

13. The method of claim 1, further comprising fitting the produced overlay to the working tooth and the neighboring tooth of the working tooth such that the determined surface of the overlay contacts the respective one or ones of the working tooth and the neighboring tooth of the working tooth to maintain the overlay in position over the working tooth during movement of the dentist cutting tool along the first and second guiding edges.

14. The method of claim 1, further comprising:

determining the predetermined part of the tooth structure to be removed from the working tooth so as to prepare the working tooth for treatment.

15. The method of claim 1, wherein the determined first and the determined second guiding edges are determined for simultaneously contacting the dentist cutting tool at contact points longitudinally distanced from each other by the distance (d) such that, when the produced overlay is produced, the first and second guiding edges define a guiding surface of contact points along which any one or any combination of the horizontal, vertical, and tilt movements of the dentist cutting tool are to be guided.

16. The method of claim 1, wherein the first and the second guiding edges define a path extending along an upper surface of the overlay and suitable for guiding the dentist cutting tool along the path in such a manner as to enable a guided removal of at least the portion of the predetermined part of the tooth structure to be removed from the working tooth.

17. The method of claim 1, wherein the dentist cutting tool comprises a cutting portion and a collar, either one or both of the first and second guiding edges being designed to contact the collar so as to enable the dentist cutting tool to be guided with a predetermined depth.

18. The method of claim 1, wherein the produced overlay is produced via any one or any combination of computer-aided manufacturing, 3-D printing, and rapid prototyping.

19. The method of claim 1, wherein the distance d is at least 0.5 mm.

20. The method of claim 1, wherein the distance d is in a range between 1 mm and 4 mm.

21. The method of claim 1, wherein the distance d is at least 4 mm.

22. A method for producing a dentist tool comprising an overlay and at least a further overlay, to be used by a dentist in guiding a dentist cutting tool in removing predetermined tooth structure to be removed from a working tooth in a plurality of stages, at least each of the overlay and the further overlay corresponding to a respective stage of removal of the tooth structure from the working tooth, at least the further overlay being provided to guide the dentist cutting tool in at least one further stage of removal of the tooth structure that is different than the stage of removal of the tooth structure corresponding to the overlay, the method comprising:

simulating any of predetermined horizontal, vertical, and tilt movements to be followed by at least one dentist cutting tool in order to remove at least a portion of a predetermined part of tooth structure of the working tooth so as to prepare the working tooth for treatment;

determining an overlay with a surface configured for fitting either one or both of the working tooth and a neighboring tooth of the working tooth such that the surface, when so fitted, contacts the respective one or ones of the working tooth and the neighboring tooth of the working tooth to maintain the overlay releasably fixed in a same position over the working tooth during movement of the dentist cutting tool along first and second guiding edges of the overlay, wherein the determining comprises:

i) determining the first guiding edge within the overlay, the first guiding edge corresponding to the at least one predetermined horizontal, vertical, and tilt movements simulated; and ii) determining the second guiding edge within the overlay that is spaced apart from the first guiding edge by a distance (d), whereby the second guiding edge corresponds to the respective one or combination of the predetermined horizontal, vertical, and tilt movements simulated, the first and second guiding edges thereby being provided to contact the dentist cutting tool so as to guide the dentist cutting tool such that the dentist cutting tool follows the at least one predetermined horizontal, vertical, and tilt movements for removal of at least a portion of the predetermined part of tooth structure of the working tooth to be removed;

producing the determined overlay with the first and the second guiding edges, the produced overlay having the determined surface configured for fitting the respective one or ones of the working tooth and the neighboring tooth of the working tooth such that the determined surface of the produced overlay, when so fitted, contacts the respective one or ones of the working tooth and the neighboring tooth of the working tooth to maintain the overlay releasably fixed in the same position over the working tooth during movement of the dental cutting tool along the first and the second guiding edges;

simulating a further predetermined movement to be followed by the dentist cutting tool to remove a portion of the predetermined part of the tooth structure to be removed from the working tooth but not removed through the use of the overlay;

determining a further first guiding edge within the further overlay, the further first guiding edge corresponding to the further predetermined movement;

determining a further second guiding edge within the further overlay that is spaced apart from the further first guiding edge by a distance (d), the further second guiding edge corresponding to the further predetermined movement, the further first guiding edge and the further second guiding edge thereby being provided to contact the dentist cutting tool so as to guide a movement of said dentist cutting tool such that the dentist cutting tool follows the further predetermined movement for removal of at least a portion of the predetermined part of the tooth structure to be removed from the working tooth but not removed through the use of the overlay; and producing at least the further overlay with the further first guiding edge and the further second guiding edge.

23. The method of claim 22, wherein the overlay and the further overlay are part of a set of overlays for removing tooth structure from the working tooth for the later installation of a crown or a bridge or an onlay on the working tooth after the removal of the predetermined part of the tooth structure to be removed from the working tooth, wherein the steps of producing the overlay and producing the further overlay comprise two of the following steps i)-v):

i) producing a first overlay for guiding the dentist cutting tool to cut away at least a portion of an upper part of the working tooth based on the desired height of remaining tooth structure of the working tooth after the removal of the predetermined tooth structure to be removed from the working tooth;

ii) producing a second overlay for guiding the dentist cutting tool to cut away at least a portion of one of the longitudinal sides of the working tooth;

iii) producing a third overlay for guiding the dentist cutting tool to cut away at least a portion of a transversal sides of the working tooth;

iv) producing a fourth overlay for guiding said dentist cutting tool to round off edges between the longitudinal and the transversal sides of the working tooth at one side of the working tooth; and v) producing a fifth overlay for guiding said dentist cutting tool to round off edges between the longitudinal and the transversal sides of the working tooth at the other side of the working tooth opposite the one side of the working tooth.

* * * * *